United States Patent [19]

Iwanaga et al.

[11] Patent Number: 5,298,667
[45] Date of Patent: Mar. 29, 1994

[54] PROCESS FOR PRODUCING PHENOL AND METHYL ETHYL KETONE

[75] Inventors: Kiyoshi Iwanaga; Mitsuhisa Tamura, both of Ichihara; Toshio Nakayama; Masahiro Usui, both of Sodegaura; Hiroyuki Umida, Ibaraki; Hirooki Nagaoka, Minoo, all of Japan

[73] Assignee: Sumitomo Chemical Company, Limited, Osaka, Japan

[21] Appl. No.: 995,971

[22] Filed: Dec. 23, 1992

[30] Foreign Application Priority Data

| Dec. 26, 1991 | [JP] | Japan | 3-344976 |
| Dec. 26, 1991 | [JP] | Japan | 3-344977 |
| Jul. 8, 1992 | [JP] | Japan | 4-180768 |
| Jul. 14, 1992 | [JP] | Japan | 4-186538 |

[51] Int. Cl.$^5$ ............................................. C07C 45/53
[52] U.S. Cl. ..................................... 568/385; 568/798
[58] Field of Search ................................. 568/385, 998

[56] References Cited

U.S. PATENT DOCUMENTS

| 2,904,592 | 9/1959 | Ellis et al. | 568/385 |
| 2,957,921 | 10/1960 | Adams et al. | 568/385 |
| 4,408,083 | 10/1983 | Toyoura et al. | 568/385 |
| 4,567,304 | 1/1986 | Fulmer | 568/385 |

FOREIGN PATENT DOCUMENTS

| 2182802 | 12/1973 | France | 568/385 |
| 2183296 | 12/1973 | France | 568/385 |
| 48-80524 | 10/1973 | Japan | 568/385 |
| 63-42619 | 8/1988 | Japan | 568/385 |

OTHER PUBLICATIONS

Chemical Abs. 108:74975s (1988).

*Primary Examiner*—James H. Reamer
*Attorney, Agent, or Firm*—Cushman, Darby & Cushman

[57] ABSTRACT

Any one material selected from (A) sec-butylbenzene substantially free from ethyl hydroperoxide, carboxylic acids and phenol, (B) sec-butylbenzene substantially free from styrenes and (C) sec-butylbenzene substantially free from methylbenzyl alcohol is oxidized to obtain sec-butylbenzene hydroperoxide, which is then decomposed to obtain phenol and methyl ethyl ketone.

9 Claims, No Drawings

PROCESS FOR PRODUCING PHENOL AND METHYL ETHYL KETONE

The present invention relates to a process for producing phenol and methyl ethyl ketone. In more particular, the invention relates to a process for producing phenol and methyl ethyl ketone which uses sec-butylbenzene as a starting material.

It has already been known that phenol and methyl ethyl ketone are produced by oxidizing sec-butylbenzene to sec-butylbenzene hydroperoxide and decomposing the sec-butylbenzene hydroperoxide (JP-A-48-80524). In this prior art process, however, a liquid containing unreacted sec-butylbenzene is recovered besides a liquid containing phenol and methyl ethyl ketone. Therefore, it is desirable to reuse the unreacted sec-butylbenzene by recycling the liquid containing unreacted sec-butylbenzene to the oxidation step from the viewpoint of material utilization efficiency. However, the prior art process has the following problems. The liquid containing unreacted sec-butylbenzene contains impurities that inhibit the oxidation reaction. The recycling of such liquid containing unreacted sec-butylbenzene to the oxidation step without removing impurities undesirably accumulates the impurities in the oxidation reaction system and the accumulation of the impurities much disadvantageously reduces the oxidation reaction rate.

An example of such impurities is ethyl hydroperoxide formed as a by-product in the oxidation. It is accumulated in the reaction system and reduces the reaction rate of the oxidation. Moreover, the accumulation of ethyl hydroperoxide in the system is undesirable from the viewpoint of safety due to the explosiveness of ethyl hydroperoxide. With regard to the elimination of the by-products formed during the oxidation, there has been known a process wherein in the oxidation of cumene to cumene hydroperoxide an alkali is added to the oxidation reaction system to suppress the undesirable formation of carboxylic acids by-products (JP-B-63-42619). However, the application of this process to the oxidation system for oxidizing sec-butylbenzene to sec-butylbenzene hydroperoxide disadvantageously reduces the selectivity of the oxidation reaction.

Moreover, when the recovered liquid containing unreacted sec-butylbenzene is recycled to the sec-butylbenzene oxidation step, it is inevitably accompanied by styrenes. Styrenes are formed in the decomposition step and can be hardly removed even by the use of a distillation column with a large number of plates. They cause the problem of reducing the yield per unit time of sec-butylbenzene hydroperoxide from sec-butylbenzene (JP-A-48-80524).

Further, the recovered liquid containing unreacted sec-butylbenzene contains, besides the above-mentioned oxidation-inhibiting substances, other impurities which inhibit the oxidation such as methylbenzyl alcohol.

In recognition of the situation, the object of the present invention is to provide a process for producing phenol and methyl ethyl ketone from sec-butylbenzene through sec-butylbenzene hydroperoxide which process prevents the accumulation of undesirable by-products in the production system, permits the effective recycling and reuse of unreacted sec-butylbenzene and maintains a high level of oxidation rate.

The present inventors have made extensive study to solve the above-mentioned problems and resultantly attained the present invention.

According to the present invention, there is provided a process for producing phenol and methyl ethyl ketone which comprises the steps of:

(I) oxidizing one material selected from the group consisting of:

(A) sec-butylbenzene substantially free from ethyl hydroperoxide, carboxylic acids and phenol, (B) sec-butylbenzene substantially free from styrenes, and (C) sec-butylbenzene substantially free from methylbenzyl alcohol, to obtain sec-butylbenzene hydroperoxide, and (II) decomposing the sec-butylbenzene hydroperoxide to obtain phenol and methyl ethyl ketone. described below firstly with the case wherein (A) sec-butylbenzene substantially free from ethyl hydroperoxide, carboxylic acids and phenol is selected as the starting material. That is, description is given of a process for producing phenol and methyl ethyl ketone wherein the step (I) includes the step of selecting (A) sec-butylbenzene substantially free from ethyl hydroperoxide, carboxylic acids and phenol, as the starting material.

The process comprises the steps of:

an oxidation step (A1): oxidizing sec-butylbenzene substantially free from ethyl hydroperoxide, carboxylic acids and phenol to obtain a reaction liquid containing sec-butylbenzene hydroperoxide as the main product, and an exhaust gas, a condensation step (A2): cooling the exhaust gas obtained in the oxidation step (A1) to obtain a condensate containing sec-butylbenzene, ethyl hydroperoxide, carboxylic acids and phenol, a concentration step (A3): concentrating the reaction liquid obtained in the oxidation step (A1) by means of distillation to obtain a bottom liquid containing sec-butylbenzene hydroperoxide as the main component from the column bottom and a distillate containing sec-butylbenzene, ethyl hydroperoxide, carboxylic acids and phenol from the column top, an alkali-washing step (A4): washing the condensate obtained in the condensation step (A2) and the distillate obtained in the concentration step (A3) with an aqueous alkali solution, separating them into an oil layer and an aqueous layer, and recycling the oil layer to the oxidation step (A1), the amount of the alkali in the aqueous alkali solution being within the range of 1–10 moles per mole of the total of the ethyl hydroperoxide, carboxylic acids and phenol present in the total of the condensate and the distillate and within the range of 10–100 moles per mole of the total of the carboxylic acids and phenol present in the total of the condensate and the distillate, and, a decomposition step (A5): decomposing the bottom liquid obtained by the concentration step (A3) containing sec-butylbenzene hydroperoxide as the main component to obtain phenol and methyl ethyl ketone.

The sec-butylbenzene (A) as the starting material preferably contains 0.01-5% by weight of ethyl hydroperoxide, not more than 0.01% by weight of carboxylic acids and not more than 0.001% by weight of phenol.

The oxidation step (A1) is a step of oxidizing sec-butylbenzene to obtain an oxidation reaction liquid containing sec-butylbenzene hydroperoxide as the main product. It is carried out, for example, by contacting liquid sec-butylbenzene with an oxygen-containing gas at a temperature of 90°-150° C. and a pressure of 1-10 kg/cm²G so that sec-butylbenzene is converted to sec-butylbenzene hydroperoxide.

The condensation step (A2) is a step of cooling the oxidation exhaust gas evolved in the oxidation step (A1) to obtain a condensate containing sec-butylbenzene, ethyl hydroperoxide, carboxylic acids and phenol. It can be conducted by using a conventional cooling condenser.

The concentration step (A3) is a step of concentrating the oxidation reaction liquid by means of distillation to obtain a bottom liquid containing sec-butylbenzene hydroperoxide as the main component from the column bottom and a distillate containing sec-butylbenzene, ethyl hydroperoxide, carboxylic acids and phenol from the column top. The distillate contains, besides sec-butylbenzene and ethyl hydroperoxide, also carboxylic acids and a small amount of phenol. The distillation conditions in the concentration step (A3) are chosen, in short, so as to enable to separate a bottom liquid containing sec-butylbenzene hydroperoxide as the main component from a distillate containing sec-butylbenzene, ethyl hydroperoxide, carboxylic acids and phenol. For example, the distillation is carried out at a column bottom temperature of 50°-150° C. and a column top pressure of 1-200 torr.

In the oxidation step (A1), such by-products as ethyl hydroperoxide, carboxylic acids and phenol are formed in addition to the intended sec-butylbenzene hydroperoxide. A part of these by-products are distilled out of the oxidation vessel carried by the oxidation exhaust gas together with unreacted sec-butylbenzene and are recovered in the condensate in the condensation step (A2). Further, the distillate obtained in the concentration step (A3) contains, besides sec-butylbenzene, also such by-products as ethyl hydroperoxide, carboxylic acids and phenol. The sec-butylbenzene contained in these condensate and distillate should be recycled to the oxidation step (A1) and reused as the starting material for the oxidation. However, when the condensate and the distillate which contain such by-products as ethyl hydroperoxide, carboxylic acids and phenol, are recycled to the oxidation step without removing them, the by-products are accumulated in the system and reduce the reaction rate of the oxidation step (A1), lower the volume efficiency of the reactor and cause problems in safety such as explosion. The present invention enables overcoming these difficulties. The present inventors are the first to find that the by-products such as ethyl hydroperoxide, carboxylic acids and phenol which cause these difficulties can be removed all at once with the alkali-washing step (A4) described below.

The alkali washing step (A4) is a step of washing the condensate obtained in the condensation step (A2) and the distillate obtained in the concentration step (A3) with an aqueous alkali solution, separating them into an oil layer and an aqueous layer and recycling the oil layer to the oxidation step (A1), wherein the amount of the alkali in the aqueous alkali solution is within the range of 1-10 moles per mole of the total of ethyl hydroperoxide, carboxylic acids and phenol present in the total of the condensate and the distillate and within the range of 10-100 moles per mole of the total of carboxylic acids and phenol present in the total of the condensate and the distillate. The contents of the respective by-products in the liquid subjected to the alkali washing vary depending on the operation conditions of the preceding steps. They are usually 0.1-5% by weight for ethyl hydroperoxide, 0.01-1% by weight for carboxylic acids and 0.001-0.1% by weight for phenol. The conditions of alkali washing are as follows.

The alkali used in the alkali washing is usually the aqueous solution of an alkali metal hydroxide or an alkali metal carbonate. Particularly preferred is the aqueous solution of sodium hydroxide. The amount of the alkali used is 1-10 moles, preferably 2-7 moles, per mole of the total of ethyl hydroperoxide, carboxylic acids and phenol and 10-100 moles, preferably 10-60 moles, per mole of the total of carboxylic acids and phenol. When the amount of the alkali is too small, the effect of removing by-products tends to be insufficient. When the amount is too large, to the contrary, it tends to cause loss of the alkali. The concentration of alkali in the aqueous alkali solution used is generally 1-30% by weight, preferably 3-15% by weight. When the concentration is too low, the amount of waste water tends to increase. When the concentration is too high, to the contrary, the separation to the oil layer and the aqueous layer after washing tends to become poor. The temperature of the alkali washing step (A4) is generally from ordinary temperature (ca. 20° C.) to 80° C. When the temperature is too low, the separation into 2 layers sometimes becomes poor. When the temperature is too high, the decomposition of the hydroperoxide tends to occur. The alkali washing should be conducted in practice so that, in short, the liquid to be washed is thoroughly contacted with the aqueous alkali solution and then separated into an oil layer and an aqueous layer, by using, for example, a vessel equipped with a stirrer, line mixer, pipe mixer, and the like. With the alkali washing step (A4), undesirable by-products can be separated from the oil layer very efficiently and the concentrations of by-products in the oil layer can be generally maintained at 0.01-0.5% by weight for ethyl hydroperoxide, not more than 0.01% by weight for carboxylic acids and not more than 0.001% by weight for phenol.

The intended final products, phenol and methyl ethyl ketone, can be produced by decomposing the bottom liquid containing sec-butylbenzene hydroperoxide as the main component obtained from the column bottom in the concentration step with an acidic catalyst to convert the hydroperoxide into phenol and methyl ethyl ketone and then isolating and purifying these products.

As one preferred embodiment of the present invention, a hydrogenation step (A6) and a distillation step (A7) described below may be provided after the alkali washing step (A4).

The hydrogenation step (A6) is a step of subjecting the aqueous layer obtained in the alkali washing step (A4), immediately or after neutralization, to hydrogenation for converting ethyl hydroperoxide to ethanol. The hydrogenation conditions are, for example, as follows. The catalyst can be selected from conventional hydrogenation catalysts such as palladium, platinum, ruthenium and rhodium. These catalysts may also be used after supported on a carrier such as activated carbon, silica, alumina, silica-alumina and activated clay. The reaction temperature is usually between ordinary temperature (ca. 20° C.) and 150° C., preferably between 40° and 100° C. When the temperature is too high, the control of the reaction tends to be difficult. When the temperature is too low, to the contrary, the reaction tends to proceed too slowly. The pressure is usually 1-30 kg/cm²G, preferably 1-15 kg/cm²G. When the pressure is too high, the reaction tends to be difficult to control. When the pressure is too low, the reaction tends to proceed too slowly. The amount of hydrogen supplied may be 1 mole per mole of ethyl hydroperoxide. However, hydrogen can be added in excess in order to increase the rate of hydrogenation. In such a case, the amount of hydrogen supplied is usually 1-10 moles, preferably 1-5 moles, per mole of ethyl hydroperoxide. The excess hydrogen can be recycled and reused. When the amount of hydrogen supplied is too small, the progress of hydrogenation tends to be insufficient. When the amount is too large, the amount of recycled hydrogen tends to become excessively large, which is undesirable. The reaction mode of the hydrogenation is not particularly limited. The hydrogenation may be conducted in any of the fixed bed, fluidized bed, and suspension. Thus, a hydrogenation reaction liquid containing ethanol, carboxylic acids and phenol is obtained.

The distillations step (A7) is a step of distilling the hydrogenation reaction liquid obtained in the hydrogenation step (A6) to recover ethanol from the column top. The distillation conditions are chosen so as to obtain a distillate containing ethanol as the main component and a bottom liquid containing carboxylic acids and phenol. Such conditions are, for example, at a column bottom temperature of 50°-150° C. and a column top pressure of 0.2-5 kg/cm$^2$G.

By the hydrogenation step (A6) and the distillation step (A7), ethanol can be recovered. The recovered ethanol can be effectively used as a valuable compound for various purposes. On the other hand, carboxylic acids and a small amount of phenol are recovered as the column bottom liquid and are discarded after processed in a waste water treatment step or such. A part of the discharged water can also be recycled to the alkali washing step (A4) in order to decrease the amount of waste water and to prevent the loss of the alkali added in excess.

As another preferred embodiment of the present invention, a thermal decomposition step (A8) described below is provided after the alkali washing step (A4). The thermal decomposition step (A8) is a step of subjecting the aqueous layer obtained in the alkali washing step (A4), immediately or after neutralization, to thermal decomposition to thermally decompose ethyl hydroperoxide. The thermal decomposition is conducted in the temperature range of 80°-200° C., preferably 100°-160° C. When the reaction temperature is too high, the reaction tends to be difficult to control. When the reaction temperature is too low, the reaction tends to proceed too slowly. The pressure in the reaction should be in the range wherein ethyl hydroperoxide can be kept in the liquid phase (i.e., aqueous solution). Through the thermal decomposition, ethyl hydroperoxide is decomposed into ethanol, acetaldehyde and acetic acid. In this way hydroperoxides are eliminated, which are dangerous and destroy the microorganisms in the activated sludge for waste water treatment to reduce the activity of the sludge (cf. JP-B-63-42619). A still another preferred embodiment of the present invention involves recovering the heat of decomposition generated in the thermal decomposition with conventional heat exchangers or the like to use the recovered heat for steam generation or other suitable purposes.

Next, the process of the present invention is described with the case wherein (B) sec-butylbenzene substantially free from styrenes is selected as the starting material. That is, description is given of a process for producing phenol and methyl ethyl ketone wherein the step (I) includes the step of selecting (B) sec-butylbenzene substantially free from styrenes, as the starting material.

The process comprises the steps of: an oxidation step (B1): oxidizing sec-butylbenzene substantially free from styrenes to obtain a reaction liquid containing sec-butylbenzene hydroperoxide as the main product, a concentration step (B2): concentrating the reaction liquid obtained in the oxidation step B1) by means of distillation to obtain a bottom liquid containing sec-butylbenzene hydroperoxide as the main component from the column bottom and a distillate containing sec-butylbenzene as the main component from the column top, and recycling the distillate to the oxidation step (B1), a decomposition step (B3): contacting the bottom liquid obtained in the concentration step (B2) with an acidic catalyst for decomposing the sec-butylbenzene hydroperoxide to phenol and methyl ethyl ketone, to obtain a decomposition liquid, a neutralization step (B4): neutralizing the decomposition liquid obtained in the decomposition step (B3) with an aqueous alkali solution, separating them into an oil layer and an aqueous layer and recycling a part of the aqueous layer to the present step (B4), and a purification step (B5): subjecting the oil layer obtained in the neutralization step (B4) to distillation to separate into a fraction containing phenol as the main component, a fraction containing methyl ethyl ketone as the main component and a fraction containing sec-butylbenzene as the main component, and recycling the fraction containing sec-butylbenzene as the main component to the oxidation step B1).

The sec-butylbenzene (B) as the starting material preferably contains not more than 0.1% by weight of styrenes.

The oxidation step B1) is a step of oxidizing sec-butylbenzene to obtain an oxidation reaction liquid containing sec-butylbenzene hydroperoxide as the main product. It is conducted, for example, by contacting liquid sec-butylbenzene with an oxygen-containing gas at a temperature of 90°-150° C. and a pressure of 1-10 kg/cm$^2$G so that sec-butylbenzene is converted to sec-butylbenzene hydroperoxide.

The concentration step (B2) is a step of concentrating the oxidation reaction liquid by means of distillation to obtain a bottom liquid containing sec-butylbenzene hydroperoxide as the main component from the column bottom and a distillate containing sec-butylbenzene as the main component from the column top. The distillation conditions in the concentration step (B2) are chosen, in short, so as to enable to separate a bottom liquid containing sec-butylbenzene hydroperoxide as the main component from a distillate containing sec-butylbenzene as the main component. For example, the distillation is carried out at a column bottom temperature of 50°-150° C. and a column top pressure of 1-200 torr.

The decomposition step (B3) is a step of contacting the bottom liquid of the concentration step (B2) with an acidic catalyst to decompose sec-butylbenzene hydroperoxide into phenol and methyl ethyl ketone. The acidic catalyst used includes sulfuric acid, sulfuric anhydride, perchloric acid and phosphoric acid.

The acidic catalyst is used usually in an amount of 0.01-1% by weight. The decomposition temperature is usually within the range of 50°-100° C.

The neutralization step (B4) is a step of neutralizing the decomposition liquid obtained in the decomposition step (B3) with an aqueous alkali solution, separating them into an oil layer and an aqueous layer, and recycling a part of the aqueous layer again to the inlet of the neutralization step (B4). The alkalis used for the neutralization include the hydroxides, carbonates and bicarbonates of sodium, potassium and lithium. The alkali is used in an amount sufficient to keep the pH of the aqueous layer usually at 4–11, preferably at 4–9. Preferably, the temperature is from ordinary temperature (ca. 20° C.) to 90° C. and the weight ratio of the oil layer to the aqueous layer is 0.5–5. The neutralization step (B4) is so conducted as to make possible thorough contact of the liquid layer to be neutralized with the aqueous alkali solution and subsequent separation into the oil layer and the aqueous layer. It is carried out by using, for example, vessels equipped with a stirrer, line mixers, pipe mixers, and the like. In the neutralization step (B4), a part of the aqueous layer after having been used in the neutralization step (B4) may be recycled and used again in order to reduce the amount of waste water. When the aqueous layer is recycled, the salt concentration in the neutralization step (B4) increases resultantly; therefore, it is preferable to keep the salt concentration usually at 1–30% by weight. The oil layer obtained in the neutralizing step (B4) is transferred to the subsequent purification step. On the other hand, a part of the aqueous layer is discarded and the rest is recycled to the neutralization step (B4).

The purification step (B5) is a step of subjecting the oil layer obtained in the neutralization step (B4) to distillation to separate the oil layer into a fraction containing phenol as the main component, a fraction containing methyl ethyl ketone as the main component and a fraction containing sec-butylbenzene as the main component, and recycling the fraction containing sec-butylbenzene as the main component to the oxidation step B1). It is conducted usually by using plural distillation columns.

One of the characteristic features of the presently described process lies in that the fraction containing sec-butylbenzene as the main component recycled from the purification step (B5) to the oxidation step B1) is substantially free from styrenes. Preferred methods for removing styrenes from the fraction to be recycled are specifically described below.

One of the preferred methods comprises providing a hydrogenation step (B6) and a separation step (B7).

The hydrogenation step (B6) is a step of subjecting the fraction containing sec-butylbenzene as the main component obtained in the purification step (B5) to hydrogenation so that styrenes contained in the fraction are converted to alkylbenzenes.

The conditions for the hydrogenation are, for example, as follows.

The catalyst used can be selected from conventional hydrogenation catalysts, such as platinum, palladium, ruthenium, rhodium and the like. These metal catalysts may also be used after supported on a carrier, such as activated carbon, silica, alumina, silica-alumina, activated clay, and the like. The temperature is usually from ordinary temperature (ca. 20° C.) to 140° C., preferably 50°–100° C. When the temperature is too high the reaction tends to be difficult to control. When the temperature is too low, to the contrary, the reaction tends to proceed too slowly. The pressure is usually 5–30 kg/cm$^2$g, preferably 10–20 kg/cm$^2$G. When the pressure is too high, the reaction tends to be difficult to control. When the pressure is too low, the reaction tends to proceed too slowly. The amount of hydrogen supplied may be 1 mole per mole of styrenes, but the hydrogen can be added in excess in order to secure sufficient hydrogenation. In such a case, the amount of hydrogen supplied is usually 1–10 moles, preferably 4–7 moles, per mole of styrenes. The excess hydrogen added can be recycled and reused. When the amount of hydrogen added is too small, the progress of hydrogenation tends to be insufficient. When the amount is too large, to the contrary, the amount of recycled hydrogen tends to become excessively large, which is unfavorable. The mode of the hydrogenation reaction is not particularly limited. The hydrogenation may be conducted in any of the fixed bed, fluidized bed and suspension.

Thus, styrenes are converted into alkylbenzenes. α,β-Dimethylstyrene and α-ethylstyrene are converted through the present step into sec-butylbenzene, which is the starting material for the oxidation step B1). The sec-butylbenzene is recovered and reused via the subsequent distillation step.

The separation step (B7) is a step of subjecting the hydrogenation reaction liquid obtained in the hydrogenation step (B6) to distillation to recover sec-butylbenzene, and recycling the sec-butylbenzene to the oxidations step B1). The distillation conditions are so chosen as to enable obtaining a distillate containing sec-butylbenzene as the main component. For example, the distillation is conducted at a column bottom temperature of 50°–150° C. and a column top pressure of 1–200 torr.

According to the above-mentioned method which involves the hydrogenation step (B6) and the separation step (B7), unreacted sec-butylbenzene can be effectively reused as the starting material for the oxidation without lowering the yield per unit time of sec-butylbenzene hydroperoxide from sec-butylbenzene in the oxidation. Moreover, α,β-dimethylstyrene and α-ethylstyrene, which are compounds undesirable for the oxidation, can be converted into sec-butylbenzene and effectively used as the starting material for the oxidation. Therefore, the method is particularly advantageous from the industrial viewpoint.

The present process makes it possible to maintain the concentration of styrene contained in the sec-butylbenzene recycled from the purification step at not more than 0.1% by weight, whereas the concentration of styrenes is usually about 10% by weight in the absence of hydrogenation step.

The process of the present invention will then be described with a case wherein (C) sec-butylbenzene substantially free from methylbenzyl alcohol is selected as the starting material. That is, description is given of a process for producing phenol and methyl ethyl ketone wherein the step (I) includes the step of selecting (C) sec-butylbenzene substantially free from methylbenzyl alcohol, as the starting material.

The process comprises the steps of: an oxidation step (C1): oxidizing sec-butylbenzene substantially free from methylbenzyl alcohol to obtain a reaction liquid containing sec-butylbenzene hydroperoxide as the main product, a concentration step (C2): concentrating the reaction liquid obtained in the oxidation step (C1) by means of distillation to obtain a bottom liquid containing sec-butylbenzene hydroperoxide as the main component from the column bottom and a distillate containing sec-butylbenzene as the main component and substantially free from methylbenzyl alcohol from the column top, and recycling the distillate to the oxidation step (C1), a decomposition step (C3): contacting the bottom liquid obtained in the concentration step (C2) with an acidic catalyst for decomposing sec-butylbenzene hydroperoxide into phenol and methyl ethyl ketone, to obtain a decomposition liquid, a neutralization step (C4): neutralizing the decomposition liquid obtained in the decomposition step (C3) with an aqueous alkali solution, separating them into an oil layer and an aqueous layer, and recycling a part of the aqueous layer to the present step (C4), and a purification step (C5): subjecting the oil layer obtained in the neutralization step (C4) to distillation to separate into a fraction containing phenol as the main component, a fraction containing methyl ethyl ketone as the main component and a fraction containing sec-butylbenzene as the main component and substantially free from methylbenzyl alcohol, and recycling the fraction containing sec-butylbenzene as the main component and substantially free from methylbenzyl alcohol to the oxidation step (C1).

The sec-butylbenzene (C) as the starting material contains preferably not more than 0.1% by weight, more preferably not more than 0.05% by weight, of methylbenzyl alcohol.

The oxidation step (C1) is a step of oxidizing sec-butylbenzene to obtain an oxidation reaction liquid containing sec-butylbenzene hydroperoxide as the main product. It is conducted, for example, by contacting liquid sec-butylbenzene with an oxygen-containing gas at a temperature of 90°–150° C. and a pressure of 1–10 kg/cm$^2$G so that sec-butylbenzene is converted to sec-butylbenzene hydroperoxide.

The concentration step (C2) is a step of concentrating the oxidation reaction liquid by means of distillation to obtain a bottom liquid containing sec-butylbenzene hydroperoxide as the main component from the column bottom and a distillate containing sec-butylbenzene as the main component and substantially free from methylbenzyl alcohol from the column top, and recycling the distillate to the oxidation step (C1). The distillation conditions in the concentration step (C2) are chosen, in short, so as to enable obtaining a bottom liquid containing sec-butylbenzene hydroperoxide as the main component from the column bottom and a distillate containing sec-butylbenzene as the main component and substantially free from methylbenzyl alcohol from the column top. For example, the distillation is conducted at a column bottom temperature of 50°–150° C. and a column top pressure of 1–200 torr. The concentration of methylbenzyl alcohol contained in the distillate containing sec-butylbenzene as the main component recovered from the concentration step (C2) is maintained usually at not more than 0.01% by weight.

The decomposition step (C3) is a step of contacting the bottom liquid of the concentration step (C2) with an acidic catalyst to decompose sec-butylbenzene hydroperoxide into phenol and methyl ethyl ketone. The acidic catalyst used includes sulfuric acid, sulfuric anhydride, perchloric acid and phosphoric acid. The acidic catalyst is used usually in an amount of 0.01–1% by weight. The decomposition temperature is usually 50°–100° C.

The neutralization step (C4) is a step of neutralizing the decomposition liquid obtained in the decomposition step (C3) with an aqueous alkali solution, separating them into an oil layer and an aqueous layer and recycling a part of the aqueous layer again to the inlet of the neutralization step (C4). The alkalis used for the neutralization include the hydroxides, carbonates and bicarbonates of sodium, potassium and lithium. The alkali is used in an amount sufficient to keep the pH of the aqueous layer usually at 4–11, preferably at 4–9. Preferably, the temperature is from ordinary temperature (ca. 20° C.) to 90° C. and the weight ratio of the oil layer to the aqueous layer is 0.5–5. The neutralization step (C4) is so conducted as to make possible thorough contact of the liquid layer to be neutralized with the aqueous alkali solution and subsequent separation of the oil layer and the aqueous layer. It is carried out by using, for example, vessels equipped with a stirrer, line mixers, pipe mixers, and the like. In the neutralization step (C4), a part of the aqueous layer after having been used in the neutralization step (C4) is recycled and used again in the neutralization step (C4) in order to reduce the amount of waste water. When the aqueous layer is recycled, the salt concentration in the neutralization step (C4) increases resultantly. Therefore, it is preferable to keep the salt concentration usually at 1–30% by weight. The oil layer obtained in the neutralization step (C4) is transferred to the subsequent purification step. On the other hand, a part of the aqueous layer is recycled to the neutralization step (C4) and the rest is discarded.

The purification step (C5) is a step of subjecting the oil layer obtained in the neutralization step (C4) to distillation to separate into a fraction containing phenol as the main component, a fraction containing methyl ethyl ketone as the main component and a fraction containing sec-butylbenzene as the main component and substantially free from methylbenzyl alcohol, and recycling the fraction containing sec-butylbenzene as the main component to the oxidation step (C1). The distillation is conducted, in short, under such conditions that permit separating the oil layer obtained in the neutralization step (C4) into a fraction containing phenol as the main component, a fraction containing methyl ethyl ketone as the main component and a fraction containing sec-butylbenzene as the main component and substantially free from methylbenzyl alcohol. It is usually carried out by using plural distillation columns. The amount of methylbenzyl alcohol contained in the fraction containing sec-butylbenzene as the main component recovered from the purification step (C5) is usually maintained at not more than 0.05% by weight.

The ratio of the amount of the liquid recycled from the concentration step (C2) to the oxidation step (C1) to the amount of the liquid recycled from the purification step (C5) to the oxidation step (C1) is usually about 10:1 to about 20:1, although it may be set beyond the range in view of the operating conditions. Accordingly, the concentration of methylbenzyl alcohol in the liquid recycled into the oxidation step (C1) is usually 0.01% by weight or less.

The present invention is described in detail below with reference to Examples.

Firstly, description is given of the case wherein (A) sec-butylbenzene substantially free from ethyl hydroperoxide, carboxylic acids and phenol is selected as the starting material.

EXAMPLE A-1

In a 100-l stainless steel (SUS 304) reactor was placed 47.6 kg of a liquid mixture of sec-butylbenzene substantially free from ethyl hydroperoxide, carboxylic acids and phenol, and sec-butylbenzene hydroperoxide. The content of sec-butylbenzene hydroperoxide in the mixture was adjusted to 1.1% by weight. Into the liquid mixture was introduced with stirring 80 Nl/min of air which has been diluted with nitrogen so as to have an oxygen concentration of 10% by volume. Then, the oxidation was conducted at a pressure of 1.5 kg/cm²G and a temperature of 120° C. for 6 hours.

After completion of the oxidation, the reaction liquid in the reactor was analyzed. The analysis showed that the reaction liquid had a hydroperoxide concentration of 10.7% by weight. The condensation of the oxidation exhaust gas gave 7.2 kg of a condensate. The analysis of the condensate showed that the condensate contained besides sec-butylbenzene as the main component 0.54% by weight of hydroperoxides (in terms of ethyl hydroperoxide; the same applies hereinafter), 259 ppm of phenol and 7.2 mmoles/kg of carboxylic acids (76 ppm by weight of formic acid and 339 ppm by weight of acetic acid). Then, 60 g of the condensate and 12 g of a 1N aqueous sodium hydroxide solution were placed in a 100-ml glass flask and mixed by stirring with a stirrer for 30 minutes while being heated in a warm bath at 40° C. The resulting mixture was then allowed to stand for 30 minutes and separated into an oil layer and an aqueous layer. The analysis of the oil layer showed that the oil layer contained 0.1% by weight of hydroperoxides, 5 ppm of phenol and no detectable carboxylic acids. The content of hydroperoxides in the aqueous layer was 1.9% by weight.

The results obtained in this Example are summarized as follows.

Amount used of alkali:

NaOH/(ethyl hydroperoxide+carboxylic acids+phenol)=2.1 (in molar ratio),

NaOH/(carboxylic acids+phenol)=20 (in molar ratio).

Removal efficiency of by-products in condensate by alkali washing:

Ethyl hydroperoxide: $(1-0.1/0.54) \times 100 = 81(\%)$,

Phenol: $(1-5/259) \times 100 = 98(\%)$.

Thus, it is demonstrated that ethyl hydroperoxide and phenol have been removed very effectively.

In the above analyses, ethyl hydroperoxide was determined by iodometry, carboxylic acids by ion chromatography (with Type IC 500 instrument, mfd. by Yokogawa Works, Ltd.; column: SCS 5-252) and phenol by liquid chromatography (column: SUMIPAX ODS A-212, 6 mmφ×15 cm L), respectively.

To the oil layer obtained above was added a small amount of sec-butylbenzene hydroperoxide as an initiator so that the resulting oil layer contained 1.6% by weight of hydroperoxides. Then, the resulting oil layer was subjected to oxidation in the same manner as described above. As a result, it was revealed that during the first 2 hours, the oxidation rate was approximately the same as that of the preceding oxidation described above, and that no decrease in the oxidation rate was observed.

COMPARATIVE EXAMPLE A-2

Concentrating the solution containing 10.7% by weight of sec-butylbenzene hydroperoxide obtained in the first oxidation of Example A-1 at a pressure of 10 torr and a column bottom temperature of 60°–70° C. gave a bottom liquid containing 67% by weight by hydroperoxides and a distillate containing sec-butylbenzene as the main component. The analysis of the distillate showed that it contained 0.12% by weight of hydroperoxides, 55 ppm of phenol and 2.8 mmoles/kg of carboxylic acids (55 ppm by weight of formic acid and 95 ppm by weight of acetic acid).

Then, 7 kg of the condensate of Example A-1, 7 kg of the distillate obtained above and 0.466 kg of a 1N aqueous sodium hydroxide solution were placed in a glass-lined vessel, stirred and mixed at 40° C. for 30 minutes and then allowed to stand for 30 minutes to separate into an oil layer and an aqueous layer. The analysis of the oil layer showed that the oil layer contained 0.15% by weight of hydroperoxides, 40 ppm of phenol and not less than 0.1 mmoles/kg of carboxylic acids.

The results obtained are summarized as follows. Amount used of alkali:

NaOH/(ethyl hydroperoxide+carboxylic acids+phenol)=0.57 (in molar ratio),

NaOH/(carboxylic acids+phenol)=5.0 (in molar ratio).

Removal efficiency of by-products in condensate by alkali washing:

Ethyl hydroperoxide=$(1-0.15/((0.54+0.12)/2)) \times 100 = 55(\%)$

Phenol=$(1-40/((229+55)/2)) \times 100 = 72(\%)$

This Comparative Example presents a case where the alkali washing was carried out using insufficient amount of alkali. In this case, ethyl hydroperoxide, phenol and carboxylic acids were not removed sufficiently.

To the oil layer obtained above was added a small amount of sec-butylbenzene hydroperoxide as an initiator so that the resulting oil layer had a hydroperoxide concentration of 1.6% by weight and then subjected to the first oxidation in the same manner as in Example A-1. As a result, it was revealed that during the first 2 hours, the oxidation rate was reduced to 66% that of the first oxidation in Example A-1. Thus, it was demonstrated that conducting the alkali washing without satisfying the limitations described above markedly reduced the oxidation rate.

EXAMPLE A-3

In a stainless steel (SUS 316) autoclave of 200 ml volume were placed 100 g of the aqueous layer obtained by being treated with the aqueous sodium hydroxide solution in Example A-1 and 0.1 g of a 5 wt % Pd on Al₂O₃ catalyst (mfd. by N. E. CHEMCAT CORP.), and subjected to hydrogenation at a hydrogen pressure of 10 kg/cm²G and a temperature of 60° C. for 3 hours. Resultantly, ethyl hydroperoxide conversion (reacted ethyl hydroperoxide/charged ethyl hydroperoxide×100) was 100% and ethanol selectivity (ethanol formed (mole)/ethyl hydroperoxide reacted (mole)×100) was 67%.

EXAMPLE A-4

The same procedures as in Example A-3 were repeated, except that the aqueous solution obtained by being treated with the aqueous sodium hydroxide solution was neutralized with aqueous sulfuric acid solution before the hydrogenation, and the reaction temperature and the reaction time were changed to 100° C. and 2 hours, respectively. Resultantly, the ethyl hydroperoxide conversion was 99% and the ethanol selectivity was 54%.

EXAMPLE A-5

In a stainless steel (SUS 316) autoclave of 200 ml volume was placed 100 g of the aqueous layer obtained by being treated with the aqueous sodium hydroxide solution in Example A-1, and subjected to thermal decomposition at a nitrogen pressure of 10 kg/cm$^2$G and a temperature of 150° C. for 1 hour. Resultantly, the ethyl hydroperoxide conversion was 100%.

EXAMPLE A-6

The same procedures as in Example A-5 were repeated, except that the aqueous layer obtained by being treated with the aqueous sodium hydroxide solution was neutralized with aqueous sulfuric acid solution before thermal decomposition and the reaction temperature and the reaction time were changed to 100° C. and 4 hours, respectively. Resultantly, the ethyl hydroperoxide conversion was 97%.

Nextly, description is given of a case wherein (B) sec-butylbenzene substantially free from styrenes is selected as the starting material.

EXAMPLE B-1

In a glass vessel was placed 100 g of a liquid mixture of sec-butylbenzene substantially free from styrenes, and sec-butylbenzene hydroperoxide. The content of sec-butylbenzene hydroperoxide in the mixture was adjusted to 2.0% by weight. Then, the liquid mixture was heated with vigorous stirring up to a liquid temperature of 120° C. and then subjected to oxidation while blowing air thereinto at a blow rate of 500 Nml/min for 7 hours. The analysis of the reaction liquid after the reaction showed that the concentration of the sec-butylbenzene hydroperoxide was 11.9% by weight.

COMPARATIVE EXAMPLE B-2

The same procedure as in Example B-1 was repeated, except that the liquid mixture to be subjected to oxidation was replaced by a liquid mixture of sec-butylbenzene and sec-butylbenzene hydroperoxide containing 5% by weight of α-ethylstyrene. Resultantly, it was shown that the reaction liquid contained 8.5% by weight of sec-butylbenzene hydroperoxide. Thus, it was demonstrated that in this Comparative Example, the yield of sec-butylbenzene hydroperoxide per unit time was very low.

REFERENTIAL EXAMPLE B-3

A vertically positioned reaction tube of 28 mm inner diameter was packed with 80 ml of a hydrogenation catalyst comprising granular alumina of average diameter of 3 mm impregnated with 0.1% by weight of palladium, and used for hydrogenation at a temperature of 80° C. and a pressure of 15 kg/cm$^2$G. The starting material used was a mixed solution containing 59.6% by weight of sec-butylbenzene, 32.4% by weight of acetophenone, 4.9% by weight of α,β-dimethylstyrene, 0.4% by weight of α-ethylstyrene and 2.7% by weight of other saturated hydrocarbons. The molar ratio of hydrogen to olefins was 5.4. The starting material was fed at a rate of 160 ml/hr and hydrogen gas was fed from the lower part of the reaction tube at a rate of 120 ml/min (as calculated at NTP). The composition of the reaction liquid after 60 hours was as follows: 64.8% by weight of sec-butylbenzene, 32.83% by weight of acetophenone, 0.07% by weight of α-methylbenzyl alcohol, 0.05% by weight of α,β-dimethylstyrene, 0.01% by weight of α-ethylstyrene and 2.7% by weight of other saturated hydrocarbons. Thus, the conversion of styrenes was 98.9%.

The reaction liquid obtained above was then fed at a rate of 150 g/hr to the middle stage of a distillation column packed with Helipac. The distillation pressure was 100 mmHg and the column top temperature was 105° C. The distillate was recovered from the column top at a rate of 100 g/hr. The analysis of the distillate showed that the distillate contained 97.08% by weight of sec-butylbenzene, 2.31% by weight of acetophenone, 0.01% by weight of α-methylbenzyl alcohol, 0.04% by weight of α,β-dimethylstyrene, 0.01% by weight of α-ethylstyrene and 0.50% by weight of other saturated hydrocarbons.

Further, a case is described below wherein (C) sec-butylbenzene substantially free from methylbenzyl alcohol is selected as the starting material.

EXAMPLE C-1

In a glass vessel was placed 150 g of a sec-butylbenzene solution containing 1% by weight of sec-butylbenzene hydroperoxide. The solution was heated to 120° C. with vigorous stirring and then subjected to oxidation over a period of 9 hours while blowing air thereinto at a rate of 150 Nml/min. The analysis of the reaction liquid after the reaction showed that the concentration of sec-butylbenzene hydroperoxide was 12.25% by weight.

EXAMPLE C-2 AND COMPARATIVE EXAMPLES C-3 AND C-4

The same procedure as in Example C-1 was repeated, except that the material shown in Table 1 were used as the liquid to be subjected to oxidation. The results obtained are shown in Table 1.

The results were as follows. In Examples C-1 and C-2, wherein sec-butylbenzene substantially free from methylbenzyl alcohol was used, the oxidation rate was high and a sufficient amount of sec-butylbenzene hydroperoxide was formed. To the contrary, in Comparative Examples C-3 and C-4, wherein sec-butylbenzene containing a considerable quantity of methylbenzyl alcohol was used, the oxidation rate was low and a sufficient amount of sec-butylbenzene hydroperoxide was not formed.

TABLE 1

|  | Example | | Comp. Example | |
| --- | --- | --- | --- | --- |
|  | C-1 | C-2 | C-3 | C-4 |
| Oxidation starting material | | | | |
| SHPO concentration (wt %)*[1)] | 1 | 1 | 1 | 1 |
| MBA concentration (wt %)*[2)] | 0 | 0.0084 | 0.0301 | 0.1067 |
| Reaction liquid after oxidation | | | | |
| SHPO concentration (wt %) | 12.26 | 12.81 | 7.41 | 5.29 |
| Relative oxidation rate*[3)] | 1 | 1.04 | 0.60 | 0.43 |

Notes*
*[1)]SHPO: sec-butylbenzene hydroperoxide
*[2)]MBA: methylbenzyl alcohol
*[3)]Relative oxidation rate: relative oxidation rate when the oxidation rate of Example C-1 was taken as 1, expressed by the ratio of the SHPO concentration in reaction liquid after oxidation to that of Example C-1.

As described above, according to the present invention, a process for producing phenol and methyl ethyl ketone from sec-butylbenzene through sec-butylbenzene hydroperoxide is provided. The process can prevent the accumulation of undesirable by-products in the production system, permits the effective recycling and reuse of unreacted sec-butylbenzene and can maintain a high level of oxidation rate.

What is claimed is:

1. A process for producing phenol and methyl ethyl ketone which comprises the steps of:

(A1) oxidizing sec-butylbenzene containing 0.01 to 0.5% by weight of ethyl hydroperoxide, not more than 0.01% by weight of carboxylic acids and not more than 0.001% by weight of phenol, by contacting liquid sec-butylbenzene with an oxygen-containing gas at a temperature of from 90° to 150° C. and a pressure of from 1 to 10 kg/cm$^2$G, to obtain a reaction liquid containing sec-butylbenzene hydroperoxide as the main product, and an exhaust gas, (A2) cooling the exhaust gas obtained in the step (A1) to obtain a condensate containing sec-butylbenzene, ethyl hydroperoxide, carboxylic acids and phenol, (A3) concentrating the reaction liquid obtained in the step (A1) by means of a distillation column to obtain a bottom liquid containing sec-butylbenzene hydroperoxide as the main component from the column bottom and a distillate containing sec-butylbenzene, ethyl hydroperoxide, carboxylic acids and phenol from the column top, (A4) washing the condensate obtained in the step (A2) and the distillate obtained in the step (A3) with an aqueous alkali solution having a temperature of from 20° to 80° C., separating them into an oil layer and an aqueous layer and recycling the oil layer to the step (A1), the amount of the alkali in the aqueous alkali solution being from 2 to 7 moles per mole of the total of ethyl hydroperoxides, carboxylic acids and phenol present in the total of the condensate and the distillate and from 10 to 60 moles per mole of the total of the carboxylic acids and phenol present in the total of the condensate and the distillate, the concentration of said alkali being from 1 to 30% by weight, wherein said alkali is an alkali metal hydroxide or an alkali metal carbonate, (A5) decomposing the bottom liquid obtained by the step (A3) containing sec-butylbenzene hydroperoxide as the main component to obtain phenol and methyl ethyl ketone.

2. The process of claim 1, which further comprises the steps of:

(A6) subjecting the aqueous layer obtained in the step (A4), immediately or after neutralization, to hydrogenation for converting ethyl hydroperoxide to ethanol, to obtain a hydrogenation reaction liquid, and (A7) distilling the hydrogenation reaction liquid obtained in the step (A6) in a distillation column to recover ethanol from the column top.

3. The process of claim 2, wherein the step (A6) includes the step of conducting the hydrogenation in the presence of a hydrogenation catalyst having a temperature of from ordinary temperature (ca. 20° C.) to 150° C. and having a pressure range of from 1 to 30 kg/cm$^2$G.

4. The process of claim 2, wherein the step (A6) includes the step of conducting the hydrogenation in the presence of a hydrogenation catalyst having a temperature of from 40° to 100° C. and having a pressure of from 1 to 15 kg/cm$^2$G.

5. The process of claim 2, wherein the step (A6) includes the step of selecting the amount of hydrogen supplied to the hydrogenation to be from 1 to 10 moles per mole of ethyl hydroperoxide.

6. The process of claim 2, wherein the step (A6) includes the step of selecting the amount of hydrogen supplied in the hydrogenation to be from 1 to 5 moles per mole of ethyl hydroperoxide.

7. The process of claim 1, which further comprises the step of:

(A8) subjecting the aqueous layer obtained in the step (A4), immediately or after neutralization, to thermal decomposition to thermally decompose ethyl hydroperoxide.

8. The process of claim 7, wherein the step (A8) includes the step of selecting the temperature of the thermal decomposition to be from 80° to 200° C.

9. The process of claim 7, wherein the step (A8) includes the step of selecting the temperature of the thermal decomposition to be from 100° to 160° C.

* * * * *